US012558266B2

(12) United States Patent
Peacham

(10) Patent No.: US 12,558,266 B2
(45) Date of Patent: Feb. 24, 2026

(54) GARMENT OR COMPRESSION GARMENT AND METHOD OF USE AND/OR MANUFACTURE THEREOF

(71) Applicant: Nicola Shillito, Hull (GB)

(72) Inventor: Alan Peacham, Hull (GB)

(73) Assignee: Nicola Shillito, Hull (GB)

( * ) Notice: Subject to any disclaimer, the term of this patent is extended or adjusted under 35 U.S.C. 154(b) by 515 days.

(21) Appl. No.: 18/082,469

(22) Filed: Dec. 15, 2022

(65) Prior Publication Data

US 2023/0190536 A1     Jun. 22, 2023

(51) Int. Cl.
*A61F 13/08*        (2006.01)
*A41H 43/00*        (2006.01)

(52) U.S. Cl.
CPC ............. *A61F 13/08* (2013.01); *A41H 43/00* (2013.01)

(58) Field of Classification Search
CPC ...... A61F 13/061; A61F 13/08; A61F 13/085; A61F 2013/0028; A61F 5/0106; A61F 5/0109; A61F 5/0123; A61F 2007/0042; A41H 43/00; A41B 11/121; A41B 11/123; A41B 11/125; A61H 2205/10; A61H 2209/00; D04B 1/265; D04B 9/52; D04B 2509/028; D10B 2509/028
USPC ....................................................... 606/201
See application file for complete search history.

(56)                References Cited

U.S. PATENT DOCUMENTS

| | | | |
|---|---|---|---|
| 3,728,875 A | 4/1973 | Hartigan et al. | |
| 3,889,494 A | 6/1975 | Patience et al. | |
| 4,745,917 A | 5/1988 | Hasty et al. | |
| 5,653,128 A | 8/1997 | Warren, Jr. et al. | |
| 6,135,974 A * | 10/2000 | Matz ..................... | A61F 13/085 |
| | | | 2/409 |
| 6,216,495 B1 | 4/2001 | Couzan et al. | |
| 2006/0189253 A1* | 8/2006 | Jones ..................... | A41C 1/003 |
| | | | 450/1 |

* cited by examiner

*Primary Examiner* — Kankindi Rwego
(74) *Attorney, Agent, or Firm* — Head, Johnson, Kachigian & Wilkinson, PC

(57)                ABSTRACT

A garment is provided that is arranged to be worn on a lower limb of a human subject and to cover a knee of the lower limb of the human subject and/or be provided at, above or below the knee of the lower limb of the human subject in use. At least one section of said garment is arranged to provide a compressive force to one or more locations on the lower limb of the human subject when worn in use. The garment is arranged such that the part of said garment that covers said knee and/or is provided at, immediately above or immediately below the knee when the garment is worn in use has at least one region that applies no compressive force to the venous vessels of the knee of the human subject or any compressive force that is applied to the venous vessels of the knee is less than or equal to about 8 mmHg.

15 Claims, 11 Drawing Sheets

GARMENT OR COMPRESSION GARMENT AND METHOD OF USE AND/OR MANUFACTURE THEREOF

CROSS-REFERENCE TO RELATED APPLICATIONS

This application claims priority to United Kingdom Patent Application No. 2118259.7, filed Dec. 16, 2021, which is incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

This invention relates to a garment, a compression garment and to a method of use and/or manufacture thereof.

2. Prior Art

Compression garments are known and are used for a variety of different purposes, including preventative and therapeutic treatments for a range of orthopaedic, vascular and medical conditions. For example, compression garments are recommended to help reduce the risk of deep vein thrombosis, varicose vein formation and control oedema associated with lymphoedema. Such garments are advised to be worn, pre- and post-surgery to reduce the risk of thrombosis, during pregnancy and during flight journeys in order to increase blood flow and reduce swelling by decreasing available space on the limb for tissue fluid accumulation. In addition, they are increasingly employed by amateur and elite athletes to enhance physical performance and recovery.

The success of the above garments is fundamentally related to their ability to support the circulatory system. This is based largely on the fact that if external compression pressure on a user's limb exceeds the local intravenous pressure, this narrows the local cross sectional area of the vein, thereby increasing proximal venous blood flow to the heart and also enhancing the closure of the internally located venous valves to reduce retrograde blood flow distally towards the feet. In combination this coupling effect of the garment on the venous system serves to reduce venous stasis (venous slowing) and blood pooling, known leading risk factors for venous pathologies such as deep vein thrombosis [Partsch & Partsch, 2005; Lim & Davies, 2014].

In order to reflect and support intravenous pressure differences that naturally occur in the lower limbs of a person, it is common for compression garments to include a graduated compression system. This graduated compression system has traditionally taken the form of providing relatively greater compression around a person's ankles with decreasing compressive force applied towards an upper part of a person's legs as described in U.S. Pat. No. 4,745,917. However, more recently, evidence is emerging towards the benefits of a progressively graduated profile [Mosti & Partsch et al., 2011; Couzan et al., 2012] providing relatively less pressure in the ankle region but increased pressure on the lower leg, with the greatest compressive forces provided across the calf muscles as disclosed in U.S. Pat. No. 6,216, 495.

However, irrespective of any pressure profile employed, if excessive garment pressure is applied to certain anatomical regions of the lower limb, this can reverse any beneficial effects and can result in detrimental, permanent and potentially fatal complications. Primarily, over-constriction of local blood vessels can significantly reduce or completely occlude proximal blood flow towards the heart, which if sustained can be both limb and life threatening. As a secondary consequence, this can cause a build-up of venous blood (venous congestion) below the anatomical level of internal blockage, which directly raises the distal intravenous pressure in the direction towards the feet, resulting in further blood flow restrictions. This can lead to swelling of distal peripheral veins, tearing of the inner cell wall of veins, increasing risks of venous inflammation (phlebitis), fatal blood clot formations (thrombosis), tissue necrosis and pulmonary embolism. In addition, it can cause pain and discomfort for a wearer of the garment.

Previous studies have shown that lower limb compression therapies that incorporate pressure around a user's knee joint in both healthy and pathological patients, irrespective if the remainder of the limb is compressed or not, can lead to significant major blood vessel occlusion at the popliteal vein, thus substantially increasing the iatrogenic risk of potentially fatal venous pathologies [Husni et al., 1968]. In particular, the knee region has been found to be the most acutely reactive and pressure sensitive anatomical location on the human leg [Husni et al., 1968; Thirsk et al., 1980; Kamm, 1982]. Accordingly, recommendations have been made that pressure does not exceed 10 mmHg across the knee joint, or compression should not extend across the knee, but stop below the knee joint [Husni et al., 1968]. Many compression garments do not extend across the knee but stop directly below or at the knee or provide a relative reduction in pressure towards and/or across the knee. However, since many lower limb compression garments are designed and manufactured to target, support and enhance the entire venous circulation system, pressure coverage directly below, at and above the knee is still perceived to be clinically important in order to provide continuation of pressure support to all areas of the limb [Buhs et al., 1999]. Some compression garments that have been tested within the research have shown to generate dangerously high pressure across the knee ranging from 10-23 mmHg, far above the recommended maximum pressure thresholds for this anatomical location. In consequence, many lower limb compression garments fail to adequately support the unique and vulnerable structures below, at and above the human knee, thereby significantly reducing the comfort and effectiveness of the same and which could still prove fatal to a wearer.

Due to the unique and diverse anatomically exposed structures at the knee, it has also been found that the maximum pressure threshold applied by external compression at the knee that is safe for an individual is individually specific and different at different anatomical locations around the knee. Moreover of clinical concern, despite previous blanket recommendations that pressure does not exceed 10 mmHg across the knee, multiple studies have repeatedly demonstrated significantly reduced blood flow effects in subjects and/or patients employing external compression that incorporated pressure values well below 10 mmHg forces directly below, across and directly above the human knee. Equally, advice relates to compression not crossing the knee joint, but terminating directly below, or at the knee, such as with below knee or knee high garments, or above knee garments such as compression shorts. However, detrimental compression effects are further exacerbated by the fact in these anatomical regions with large underlying bony irregular prominences acting as rigid interfaces, coupled with relatively low levels of overlying protective soft tissue musculature the pressure sensitive popliteal vein as it courses its tortured path on entry below and exit above the knee joint is highly exposed and vulnerable. It is for this reason, in particular, external compression applied in the region directly between the upper calf and below the knee represents an anatomical danger zone, highly vulnerable to 'constrictive throat effects'. This phenomenon in the presence of LOW external pressure involves the local veins directly below the knee collapsing first, inducing a constrictive throat, which not only reduces venous blood flow but begins a cascade in which the vein collapses in sequential manner distally towards the feet, increasing distal intravenous pressure and creating even greater blood flow restrictions [Thirsk et al., 1980; Kamm, 1982]. These effects are further compounded by the position of the garter, often distinct in material and whilst designed to provide relatively larger localised circumferential pressure than the remainder of the garment to keep the item in place, garters in close proximity to the knee can inadvertently behave as tourniquets [Lewis et al., 1976; Scurr et al., 2001; Lord & Hamilton, 2004] further inducing 'constrictive throat effects' on both the popliteal vein and other critical neurovascular structures surrounding the knee and increasing risks of serious venous pathologies [Scurr et al., 2001].

An example of a compression garment is disclosed in U.S. Pat. No. 5,653,128. The garment is a self-supporting sock for providing improved blood circulation in the legs of the user. The sock is formed from knitted fabric and includes an elastic band that is provided around the top of the sock and a V-shaped or U-shaped notch is formed in the elastic band extending towards the sock heel portion for the full length of the elastic band. In particular, the document states that the notch is arranged to sit on the calf of the leg of the user to remove the circumferential pressure around the calf portion of the leg. However, contemporary published research has since discovered the calf portion of the leg to be much greater pressure tolerant and is therefore able to withstand a high degree of circumferential pressure to that of the regions directly below, at and above the human knee. Moreover, it has also been repeatedly demonstrated that the degree of beneficially increased blood flow and therefore improved functionality of a compression garment is directly and positively associated to the degree of increasing calf muscle pressure [Mosti & Partsch et al., 2011; Couzan et al., 2012; Dermont et al., 2015].

A further example of a prior art product is shown in U.S. Pat. No. 3,889,494, which is in the form of a stocking with compensated knee pressure. The full length stocking is formed from knitted fabric including elastomeric yarn, which exerts a compressive effect on a wearer's leg. In the knee region the compressive effect is reduced but still providing substantial pressure support and typically in the region of less than 10 mmHg, which is between 20-80 percent less than the pressure below the knee area. This is said to reduce pressure in the popliteal space of the knee. The pressure above the knee is increased and thereafter gradually decreasing to the top of the stocking. Although this document recognises the problems associated with excessive pressure in the knee region of a human subject, there is insufficient explanation as to how the garment is to accurately and reproducibly achieve the reduced knee pressure. The garment is still likely to generate too much compressive force in specific anatomical regions directly below, at and above the knee, such as for example the vulnerable popliteal vein as it courses its tortured path across the popliteal space. Moreover, multiple independent research has demonstrated significantly reduced limb blood flow using compression pressures directly below [Litter & Wood, 1954; Spiro et al., 1970; Sabri et al., 1971; Zicot et al., 1977; Mayrovitz & Sims, 2003], across [Campion et al., 1968; Sigel et al., 1975; Gaylarde et al., 1993; Fromy et al., 1997] and directly above the knee [Mayrovitz 1998], despite deemed within the considered safe 10 mmHg upper threshold limit depicted in U.S. Pat. No. 3,889,494. Indeed, pressures ranging only between 5 mmHg and 10 mmHg in proximity to the human knee have consistently shown can be excessive enough to dangerously impede limb blood flow to devastating degrees [Litter & Wood, 1954; Campion et al., 1968; Spiro et al., 1970; Sabri et al., 1971; Sigel et al., 1975; Fromy et al., 1997; Gaylarde et al., 1993; Mayrovitz, 1998; Mayrovitz & Sims, 2003], in some cases up to 62.5% [Litter & Wood, 1954] and 70% [Gaylarde et al., 1993], substantially increasing risks of major venous complications. It has also been shown, whilst venous collapse occurs first in proximity to the knee, inducing flow limiting 'constrictive throat effects' [Kamm, 1982] initiation of such venous collapse in detriment to venous blood flow can also occur at a much lesser threshold than is appreciated by U.S. Pat. No. 3,889,494, and this can occur between 5 mmHg and 10 mmHg external pressure [Litter & Wood, 1954; Zicot & Parker, 1977; Thirsk et al., 1980].

Furthermore, although U.S. Pat. No. 3,889,494 cites the fact that the leg diameter of a user is a major factor towards calculating the amount of pressure generated by the stocking, it fails to account for sufficient internal anthropometric/anatomical factors which are highly variable between individuals. These factors can also be transiently affected as a result of, for example, tissue, muscle and/or joint swelling and/or inflammation and/or disease such as arthritis, which can increase the internal diameter of a user's limb post manufacture or application of the stocking and exacerbate pressure related problems particularly at the vulnerable region of the knee. U.S. Pat. No. 3,889,494 also inadequately addresses the fact that intravenous pressures are varied by, differing postures, activity levels, anthropometric differences and internal swelling between individuals. Furthermore, given that it is known that the region directly below, at or above the human knee shows the greatest pressure sensitivity to even very low pressures, coupled with the fact that the popliteal region of the knee in particular is a known area for fluctuating levels of daily swelling, the stocking may cause significant complications to restricting blood flow in the user. Thus the stocking may actually cause more unintentional harm to a user than benefit.

In consequence, many lower-limb garments fail to adequately support the unique and vulnerable venous and neurovascular structures below, at and above the human knee, thereby significantly reducing the comfort and effectiveness of the same, and which could still prove fatal to the wearer, as continues to be documented throughout the published research [Merret & Hanel, 1993]. A further example of a compression garment is disclosed in U.S. Pat. No. 3,728,875, wherein a stocking is shown having a garter and wherein a portion of the garter that covers the plexus of deep and superficial blood vessels in the inner thigh is replaced with a soft fabric. Whilst U.S. Pat. No. 3,728,875 attempts to support the proximal aspect of the vascular system in proximity to the upper thigh, it fails to appreciate the substantial risks associated with the more distal venous system below, across and above the knee, which directly influences the overall volume of proximal blood flow. This may account for the continued inadvertent severe and fatal ischaemic complications that continue to be highlighted within patients specifically using the same [Merret & Hanel, 1993]

It is an aim of the present invention to provide a garment or compression garment that overcomes the abovementioned problems.

It is a further aim of the present invention to provide a method of using and/or manufacturing a garment or compression garment that overcomes the abovementioned problems.

It is a further aim of the present invention to provide an alternative garment and/or method of using and/or manufacturing the same that produces significantly reduced pressure in a knee region of the garment or knee area of a user wearing the garment.

It is a yet further aim of the present invention provide a garment and/or method of using and/or manufacturing the same that more specifically and successfully targets anatomical regions of the knee known to be particularly sensitive to compressive force.

It is a yet further aim of the present invention to provide a lower limb garment or compression garment, or a compression garment wherein at least a portion of the garment is arranged to cover the knee and/or is provided adjacent the knee of a human subject when worn in use, which overcomes the abovementioned problems.

It is a yet further aim of the present invention to provide a method of using a lower limb garment or compression garment, or a compression garment wherein at least a portion of the garment is arranged to cover the knee and/or is provided adjacent the knee of a human subject when worn in use, which overcomes the abovementioned problems.

BRIEF SUMMARY OF THE INVENTION

According to a first aspect of the present invention there is provided a garment; at least part of said garment is arranged to be worn on a lower limb of a human subject and to cover a knee of the lower limb of the human subject and/or be provided at, above or below the knee of the lower limb of the human subject in use; at least one section of said garment is arranged to provide a compressive force to one or more locations on the lower limb of the human subject when worn in use; characterised in that: the garment is arranged such that the part of said garment that covers said knee and/or is provided at, above or below the knee when the garment is worn in use has at least one region that applies no compressive force to the venous vessels of the knee of the human subject or any compressive force that is applied to the venous vessels of the knee is less than or equal to about 8 mmHg.

Thus, although the prior art disclosures are acknowledged herein, none of the prior art documents teach to there being zero compressive force at, over or adjacent the venous vessels of the knee of the human subject, or being a specific reduced level of compressive force of equal to or less than about 8 mmHg. The compressive force of 0-8 mmHg of the garment is a novel and inventive subset of the prior art disclosures which is very specifically targeted to the region of the venous vessels of the knee when the garment is worn in use, which still allows the remaining regions (i.e. other than the at least one region) of the garment to apply compressive force if required to the lower limb and takes into account all the known research on the vulnerable pressure areas in and around the human knee.

Preferably the zero compressive force or the reduced compressive force of less than or equal to about 8 mmHg is provided immediately above or immediately below the knee of the human subject in use.

Preferably the compressive force applied to the region of the venous vessels by the garment is 0 to about 7 mmHg (i.e. less than or equal to about 7 mmHg).

Further preferably the compressive force applied to the region of the venous vessels by the garment is 0 to about 6 mmHg (i.e. less than or equal to about 6 mmHg).

Preferably the compressive force applied to the region of the venous vessels by the garment is 0 to about 5 mmHg (i.e. less than or equal to about 5 mmHg).

In one embodiment reference to the venous vessels of the knee include any or any combination of the popliteal vein in the popliteal space of the human subject, the short and/or long saphenous vein of the human subject, the medial and/or lateral gastrocnemius veins of the human subject and/or the like.

In one embodiment, in addition to the zero or reduced compressive force provided by the garment on the venous vessels of the knee of the human subject, the garment also provides a zero or reduced compressive force of about 8 mmHg or less on the neural structures in, around and/or associated with the knee of the human subject, such as for example, the common peroneal nerve.

In one embodiment the at least one section of the garment arranged to provide the compressive force provides a force that is greater than about 8 mmHg on the lower limb of the human subject, and particularly the area of the human subject immediately under or adjacent the at least one section of the garment, when the garment is worn in use.

In one embodiment the at least one region of the garment arranged to apply the zero compression or applying the reduced compression is provided on a posterior, medial and/or lateral region or knee region of the garment. This preferably conforms to the posterior, medial and/or lateral areas of the knee of the human subject when the garment is worn in use.

In a preferred embodiment the at least one region of the garment arranged to apply the zero compression or applying the reduced compression is provided on a posterior knee region of the garment immediately adjacent the popliteal vein in the popliteal space.

In one embodiment the at least one region of the garment consists of or includes at least one notch, aperture or cut out in the material of the garment and/or the garment includes a cuff, band or garter that is to be worn on the lower limb of the human subject in use and the at least one region of the garment consists of or includes a first portion of the cuff, band or garter that is further away from the knee of the human subject compared to a second portion of the cuff, band or garter. Either or a combination of these features incorporated into the garment of the present invention helps to provide the zero compression or reduced compression at or adjacent the knee of the human subject.

Thus, in one embodiment the cuff, band or garter of the garment is stepped, corresponding to a step in anatomical height when worn by a subject, with the region having the zero or reduced compressive force comprising the first portion of the cuff, band or garter that is further away from the knee than the second portion of the cuff, band or garter.

In one embodiment the garment includes a cuff, band or garter with at least one notch, aperture or cut out in the material of the cuff, band or garter. In one example, the cuff, band or garter is provided at the same height in the garter or anatomical height of the garment when the garment is worn in use.

In one embodiment the cuff, band or garter comprises or consists of the at least one section of the garment arranged to provide a compressive force, and preferably a compressive force of greater than 8 mmHg.

In one embodiment the cuff, band or garter is stepped, multi-level or provided at an angle with respect to the knee.

According to a further aspect of the present invention there is provided a garment; at least one section of said garment is arranged to provide a compressive force to one or more locations on a lower limb of a human subject when worn in use, or said at least one section is arranged to provide a relatively greater compressive force at said one or more locations on the human subject compared to at least one other section of said garment when worn in use; and wherein at least part of said garment is arranged to be worn on a lower limb of the human subject and to cover a knee of the human subject and/or be provided at, above or below the knee of the human knee in use;

characterised in that the at least one section of said garment providing the compressive force or the relatively greater compressive force:

a) has at least one notch, aperture or cut-out defined in said section at and/or immediately adjacent a posterior region of said garment section which is arranged so as to correspond or substantially correspond to a posterior area of a knee of a person wearing said garment in use; and/or b) is arranged such that when the garment is worn by the human subject in use, the least one section of said garment providing the compressive force or the relatively greater compressive force is provided closer to the knee of the human subject at an anterior region of the garment compared to a posterior region of the garment.

The provision of the notch, aperture or cut-out in the posterior knee region of the garment in the section of garment providing compression or a relatively higher level of compression compared to at least one other section of the garment, significantly reduces the compressive pressure and/or circumferential pressure applied to this part of a user's knee in use. This reduces or prevents the problems associated with excessive pressure in this posterior part of the knee and provides improved ventilation to the wearer of the garment.

The provision of the compressive force or relatively greater compressive force in the anterior region of the garment compared to the posterior region of the garment reduces the compressive forces around the posterior of the knee of the user, thereby reducing or preventing problems associated with excessive pressure on the knee and provides improved comfort to the wearer of the garment. The compressive forces applied by the garment in the knee region can be stepped, multi-level or provided at an angle with respect to the knee.

It will be appreciated that the two different aspects of the present invention of: a) the notch, aperture or cut-out in the posterior region of the garment, and b) the difference in anterior to posterior compression and/or the stepped/multi-level nature of compression, cuff, garter or band in the knee region of the garment, can be used independently of each other in a garment or can be used in combination together in a garment. Independently, the concepts provide independent solutions to the same problem of excessive knee pressure and, combined, the concepts provide a synergistic solution to the problem of excessive knee pressure. In fact, either concept solution alone can, in some cases reduce the pressure or compressive forces around the knee area to zero or near zero.

Furthermore, the present invention has the advantage that as well as providing a lowering of pressure across the knee as a whole (i.e. 360 circumferential reduced compressive force), the garment specifically targets a reduction in pressure at specific anatomical structures of the knee, such as at the popliteal vein at the centre immediately above and below the posterior area of the knee. This creates an anatomically undulated knee pressure system, with relatively higher and relatively lower compressive forces applied by the garment on the wearer in direct response to the specific underlying anatomical structures located at or adjacent the wearer's knee.

Preferably the garment is for wearing on one lower limb of the subject and further preferably on both lower limbs of the subject in use.

Preferably the garment is arranged to provide the compressive force or a relatively greater compressive force to the anterior area of a user's knee compared to a posterior area of the user's knee at the same circumferential height or distance at, above and/or below the knee.

In one embodiment the at least one section of said garment arranged to provide the compressive force or the relatively greater compressive force is or includes a cuff, band or garter.

Preferably the cuff, band or garter is arranged to provide an outer perimeter, circumferential or substantially circumferential compressive force on the lower limb of the subject in use.

In one embodiment the cuff, band or garter is continuous or substantially continuous in perimeter or circumference in the garment, thereby providing continuous or substantially continuous compressive force around the circumference or outer perimeter of a user's lower limb when the garment is worn in use.

In a preferred embodiment the cuff, band or garter is non-continuous in circumference, such that any compressive force provided by the cuff, band or garter of the garment to a user is non-continuous.

Preferably the at least one notch, aperture or cut-out is defined in the at least one section providing the compressive force, the relatively greater compressive force, the cuff, band or garter.

In one embodiment the at least one notch, aperture or cut-out also extends in the garment beyond the at least one section providing the compressive force, the relatively greater compressive force, the cuff, band or garter.

Preferably at least part of the at least one notch, aperture or cut-out defined in the garment is shaped such that it has a narrowing taper in the direction away from the knee region of the garment or away from a user's knee when the garment is worn in use. Thus, in one example, the width of the notch, aperture or cut out is wider closer to the knee region than it is with increasing distance away from the knee region.

In one embodiment the at least one notch, aperture or cut out is V-shaped, substantially V-shaped, U-shaped or substantially U-shaped.

Preferably the widest part of the V or U shape is closest to the posterior knee region of the garment and the apex or base of the V or U shape is furthest from the posterior knee region of the garment.

In one embodiment the at least one section providing the compressive force, the relatively greater compressive force, the cuff, band or garter includes two or more anterior portions (or relatively anterior portions) that are arranged to be on opposing but equal or substantially equal anatomical plane heights in use and situated in the anterior region of the garment when worn adjacent an anterior area of a user's knee.

In one embodiment the at least one section providing the compressive force, the relatively greater compressive force, the cuff, band or garter includes two or more posterior portions (or relatively posterior portions) that are arranged to be on opposing but equal or substantially equal anatomical plane heights in use and situated in the posterior region of the garment when worn adjacent a posterior area of a user's knee.

Preferably the anterior portions are closer to the knee region of the garment compared to the posterior portions (i.e. the anterior portions sits closer to the knee area of the user when the garment is worn by a user).

In one embodiment the at least one section providing the compressive force, the relatively greater compressive force, the cuff, band or garter includes two or more intermediate portions that are provided intermediate the anterior portions and posterior portions on opposing sides of the garment.

Preferably the two or more intermediate portions are arranged to be on opposing but equal or substantially equal anatomical plane heights when the garment is worn by a user in use.

Preferably the two or more opposing intermediate portions are arranged to be provided at the same or substantially the same angles relative to their respective anterior and/or posterior portions. Thus, in one example, both intermediate portions are arranged to be equally or substantially equally angulated obliquely to provide a step change in the anatomical plane height between the anterior portions and the posterior portions.

Preferably the angle of the two opposing intermediate portions is approximately 20-70 degrees+/−5 degrees relative to an edge of the anterior portion closest to the knee region of the garment in use, and further preferably 30-45 degrees+/−5 degrees relative to an edge of the anterior portion closest to the knee region of the garment in use.

In one embodiment the two or more anterior portions join or are integral together in the anterior region of the garment.

In one embodiment the two or more posterior portions do not join together and are a spaced distance apart from each other to define the notch, aperture or cut-out therebetween.

In one embodiment the notch, aperture or cut-out defined in the garment does not have any material in, associated with and/or over the same.

In one embodiment the notch, aperture or cut-out defined in the garment has material in, associated with and/or over the same which provides no compressive force or a compressive force of less than or equal to about 8 mmHg.

Preferably the notch, aperture or cut out provided between the posterior portions is V-shaped or substantially V-shaped in a vertical direction or in a direction transverse, perpendicular or substantially perpendicular to a top edge of the garter, band or cuff, with the apex of the V shape a spaced distance from the posterior portions. Thus, in one example the V-shape extends beyond the level of the garter, band or cuff.

Preferably an edge of the anterior portions furthest from the knee is separated from an edge of the posterior portions closest to the knee such that the respective edges are not in the same horizontal anatomical plane or at the same height when the garment is worn by a user in use.

In one example, the distance between the anterior portion edge furthest from the knee (i.e. a lower edge of the anterior portion) and the posterior portion edge closest to the knee (i.e. a higher edge of the posterior portion) is equal to or greater than 1 mm.

Preferably the height of the band, cuff, garter, anterior portions, the intermediate portions and/or the posterior portions is approximately 0.5 cm-7.65 cm+/−0.2 cm, and further preferably is approximately 1.5 cm-3 cm+/−0.2 cm. The height typically corresponds to the vertical distance or anatomical height when the garment is worn in use.

Preferably the height of the notch, aperture or cut out between the posterior portions that further preferably extends beyond the posterior portions is approximately 0.5 cm-15 cm+/−0.2 cm. The height typically corresponds to the a vertical distance or anatomical height when the garment is worn in use.

In one embodiment the at least one section of the garment providing the compressive force, the relatively greater compressive force, the cuff, the garter or band is provided adjacent or immediately adjacent the knee of a person when worn. In one embodiment the garment is designed to be worn at, adjacent or below the waist of a user and extend to a location above the knee of a user or over the knee of a user. In one example the garment can extend to the knee of a user, below the knee of a user, to the ankle of the user, over the ankle of the user or to a location between the ankle and knee of a user.

Preferably the compressive force exerted by the at least one section of the garment on one or more parts of the human body can be any or any combination of uniform, substantially uniform, graduated, substantially graduated, progressive or substantially progressive.

Preferably the garment can be used for any purpose, such as medical, sporting, leisure, shapewear and/or the like.

Preferably reference to a garment with compression or compression garment herein refers to any garment designed to exert some degree of tensile force on one or more parts of the human body when worn on the human body in use.

Preferably reference to a lower limb compression garment is a garment worn at least up to and/or below the waist of a human subject. It will be appreciated that the garment may also cover one or more other areas of the human body above the waist, providing that at least part of the garment covers at least part of at least one of the lower limbs of a human subject. For example, the garment may include a sock; a sock over, above or below the knee; a compression sock; a calf muscle sleeve, support or brace; a knee sleeve, support or brace; a thigh sleeve, support or brace; a lower limb sleeve, support or brace; a lower limb stocking, tights, body suit, body stocking, tri-suit, shorts and/or the like.

In one embodiment the notch, aperture or cut-out defined in a posterior region of the garment is immediately adjacent a posterior area of the user's knee when the garment is worn, and further preferably is provided over the popliteal fossa area of the user's knee when the garment is worn in use. Further preferably the garment in this embodiment covers the knee when worn in use.

In one embodiment the notch, aperture or cut-out in the garment or in a knee covering garment is diamond shaped or substantially diamond shaped. The diamond shape is designed to reflect the shape of the popliteal area of the knee where highly vulnerable neurovascular structures are present. The notch, aperture or cut out significantly reduces the compressive forces present in the popliteal area of a user's knee in use.

Preferably the inferior and/or superior aspects of the notch, aperture or cut out has at least one further cut out or notch defined in the same; or the inferior and/or superior aspects of the notch, aperture or cut-out extends a greater distance in the garment in the inferior and/or superior directions than the notch, aperture or cut-out extends in the proximal and/or lateral aspects of the garment. Thus, in one example, the size or length of the notch or space in the vertical or upright direction is greater than in the transverse or horizontal direction. The further inferior and/or superior notch, aperture or cut out remove further circumferential pressure on the neurovascular structures at the lower aspect of the knee and/or upper aspect of the calf, or the upper aspect of the knee and/or lower aspect of the thigh, areas of which have been shown to be vulnerable to external compressive material forces.

In one embodiment the notch, aperture or cut out is covered or substantially covered by a material that is different to the material in which the notch, aperture or cut-out is formed. In this example, the skin of a user through the notch, aperture or cut-out may not be immediately and directly contactable.

In one example, the length and/or width of the notch, aperture or cut out ranges from approximately 1 cm-4 cm+/−0.5 cm.

In one example, the inferior and/or superior notch, aperture or cut out is approximately 0.5 cm-5 cm+/−0.5 cm in length, and further preferably 1-2 cm+/−0.5 cm in length.

Preferably the at least one section of the garment providing the compressive force or relatively higher compressive force is formed from a material or includes a material that can generate a compressive force on the wearer in use, such as for example, any or any combination of elastic fibre material, elastomeric material, Lycra®, cotton, synthetic material, elastin composite material and/or the like.

Preferably the number, orientation, density and/or tightness of the fibres of the material can be adjusted to provide the required compressive force in the garment.

In one example, the material covering and/or associated with the notch, aperture or cut-out is non-elasticated material, non-elasticated cotton, nylon, polyester, silk, meshed material, net material and/or the like.

In one embodiment the at least one section of garment providing the compressive force or relatively higher compressive force exerts a pressure on average of greater than 8 mmHg, and preferably greater than 10 mmHg According to a second aspect of the present invention there is provided a method of using and/or manufacturing a garment.

According to a yet further aspect of the present invention there is provided a method of manufacturing a garment, said garment arranged to be worn on a lower limb of a human subject and to cover a knee of the lower limb and/or be provided at, above or below the knee of the lower limb of the human subject in use; said method including the steps of providing at least one section of said garment that exerts a compressive force to one or more locations on the lower limb of the human subject when worn in use; characterised in that the method further includes the step of arranging the garment such that the part of said garment that covers said knee and/or is provided at, above or below the knee when the garment is worn in use has at least one region that applies no compressive force to the venous vessels of the knee of the human subject or any compressive force that is applied to the venous vessels of the knee is less than or equal to about 8 mmHg.

According to an aspect of the present invention there is provided a method of manufacturing a garment, said garment to be worn by a human subject in use, said method including the steps of providing at least one section of said garment to exert a compressive force to one or more locations on the human subject when worn in use, or providing said at least one section of said garment to exert a relatively greater compressive force at said one or more locations on the human subject compared to at least one other section of said garment when worn in use; providing the garment so that at least part of said garment is arranged to be worn on at least a lower limb of the human subject and to cover a knee of the lower limb of the human subject and/or be provided at, above or below the knee of the leg of the human subject in use; characterised in that the method further includes the step of arranging the garment so that the at least one section of said garment providing the compressive force or the relatively greater compressive force:

a) has at least one notch, aperture or cut out defined in said section at and/or immediately adjacent a posterior region of said garment section which is arranged so as to correspond or substantially correspond to a posterior area of the knee of the human subject wearing said garment in use; and/or b) is provided closer to the knee of the human subject at an anterior region of the garment compared to a posterior region of the garment when the garment is worn in use.

According to further aspects of the present invention there is provided a compression garment and/or a method of using a compression garment.

According to yet further aspects of the present invention there is provided a lower limb compression garment and/or a method of using a lower limb compression garment.

According to one aspect of the present invention there is provided a garment which provides reduced 360 circumferential pressure around, above, immediately above, below and/or immediately below the knee of a wearer of the garment.

According to one aspect of the present invention there is provided a garment which provides zero circumferential pressure around, above, immediately above, below and/or immediately below the knee of a wearer of the garment.

The Advantages of the Present Invention Include:

a garment with a multi-level garter, cuff or band to reduce 360 degree circumferential pressures on the limb at or in the proximity of a user' knee;

an anterior portion of the garment is designed to reduce tensile force on the anterior compartment of a lower leg of a human;

the stepped nature of the material forming the garment at the posterior mid-region reduces direct circumferential force on the medial and lateral knee structures of a human subject;

the posterior element of a garter, cuff or band provided on the garment is provided on different anatomical planes to the anterior and mid region to reduce circumferential pressure on posterior structures of a user's knee in use;

the posterior aspect of the garment has a relatively small opening, notch, aperture or cut out to reduce compression force around the posterior knee area.

BRIEF DESCRIPTION OF THE DRAWINGS

Embodiments of the present invention will now be described with reference to the following figures, wherein.

DETAILED DESCRIPTION OF THE INVENTION

Figure 1A:
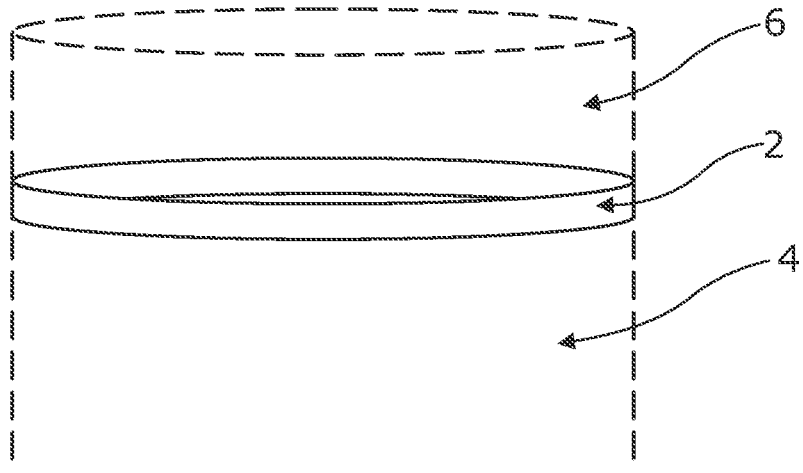
FIGS. 1a and 2a (Prior Art) show a simplified horizontal plane view and sagittal view respectively of a conventional garter, band or cuff on part of a sock garment.

Referring firstly to FIG. 1a, there is illustrated simplified views of a conventional garter 2 of a sock 4 to be worn on the lower leg 6 of a human subject. The garter 2 provides 360 degrees of uniform external circumferential pressure in the region of the lower leg just below or immediately the knee of a human subject. This relatively high uniform level of pressure around the knee has been associated with excessive pressure on internal structures of the knee, particularly in the posterior region of the knee.

Figure 1B:
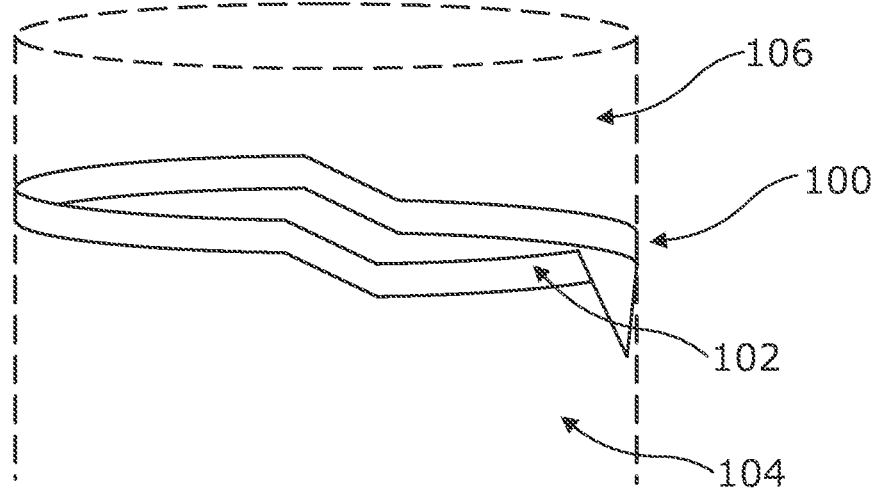
FIGS. 1b and 2b show a simplified horizontal plane view and sagittal view respectively of a garter, band or cuff on part of a sock garment according to the present invention in one embodiment.
Figure 2A:
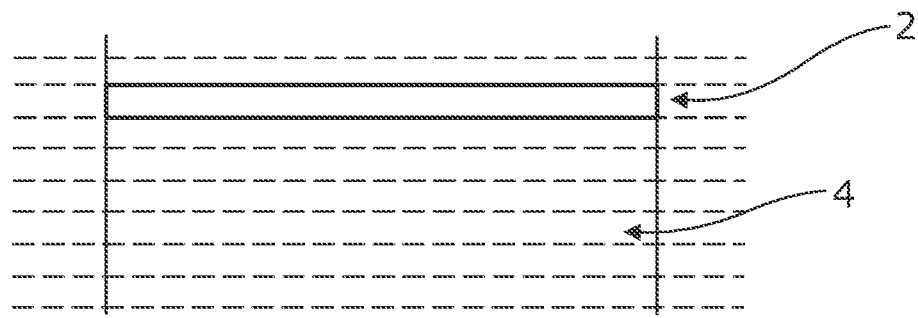
Figure 2B:
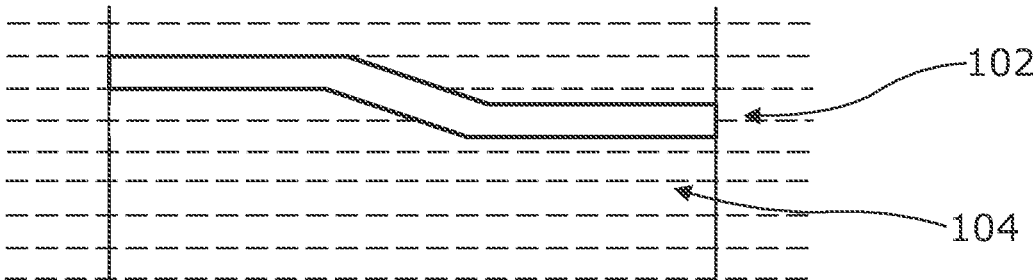

In contrast to the conventional garter, FIG. 1b shows an embodiment of the present invention 100 wherein the garter, band or cuff 102 of sock garment 104 is arranged to be stepped down in height in the anterior to posterior direction to provide a multi-level garter to be worn on the lower leg 106 of a human subject. Thus, the anterior part of the garter 102 is nearer to the knee when worn by a user compared to the posterior part of the garter 102. This results in the 360 circumferential pressure applied by the garter, band or cuff 102 around the knee being non-uniform and significantly reduced compared to the conventional garter shown in FIG. 1a, particularly in the posterior region of the same adjacent the posterior area of the knee. However, is also reduces the compressive forces in the medial and/or lateral regions of the knee.

Figure 3:
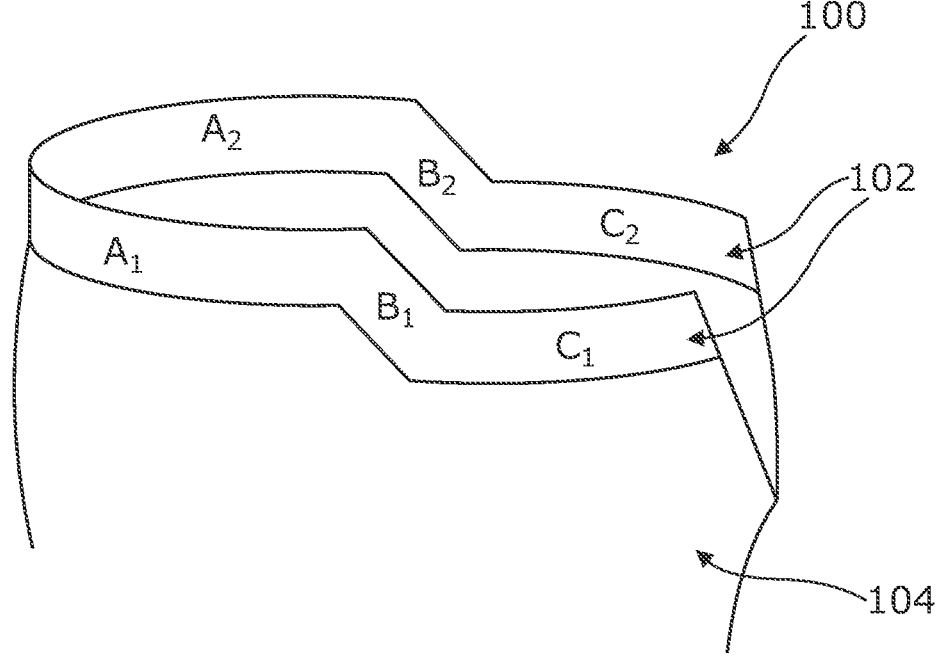
FIG. 3 is a more detailed horizontal plane view showing the different regions of the garter, band or cuff in the sock garment of the present invention in one embodiment.

Referring to FIG. 3, there is illustrated a more detailed horizontal plane view of the garter, band or cuff 102 according to an embodiment of the present invention. It can be seen than the stepped garter, band or cuff includes, in one embodiment, any or any combination of:

two anterior portions (A1 and A2) that are situated in the anterior region of the garment when worn adjacent an anterior part of the knee. The two anterior portions A1 and A2 are arranged to be on opposing but equal or substantially equal anatomical plane heights in use;

two posterior portions (C1 and C2) that are situated in the posterior region of the garment when worn adjacent a posterior part of the knee. The two posterior portions C1 and C2 are arranged to be on opposing but equal or substantially equal anatomical plane heights in use;

two intermediate portions (B1 and B2) that are provided intermediate the portions A1 and C1, and A2 and C2, respectively. The two intermediate portions B1 and B2 are arranged to be on opposing but equal or substantially equal anatomical plane heights in use;

the intermediate portions B1 and B2 are arranged to be provided at the same or substantially the same angles relative to their respective anterior and/or posterior portions. Thus, in one example, both intermediate portions B1 and B2 are arranged to be equally or substantially equally angulated obliquely to provide a step change in the anatomical plane height between the anterior portions and the posterior portions;

the posterior portions C1 and C2 of the garter 100 do not join and are a spaced distance apart from each other, thereby defining an notch, aperture or cut-out 'D' in the garter, band or cuff 100 at the posterior of the garter, band or cuff 100. Thus, there is no garment material at all present between C1 and C2, no compressive garment material present between C1 and C2, or any material present in the notch, aperture or cut out between C1 and C2 provides significantly reduced compressive force compared to the garter, band or cuff itself;

the notch, aperture or cut out provided between posterior portions C1 and C2 is V-shaped or substantially V-shaped 'E' in a vertical direction or in a direction transverse, perpendicular or substantially perpendicular to a top edge of the garter, band or cuff, with the apex of the V shape a spaced distance from the posterior portions C1 and C2. Thus, the V-shape extends beyond the level of the garter, band or cuff.

It will be appreciated that the arrangement in FIG. 3 is typically provided at the end of a garment 'F' that terminates just below the knee or just above the knee. For example, the garment could be a sock worn over the foot and calf muscle and the garter, band or cuff could be the top of the sock nearest to a user's knee; the garment could be a pair of tights or shorts that is worn over the user's thighs and the garter, band or cuff could be the bottom of the tights or shorts nearest to a user's knee.

Figure 4:
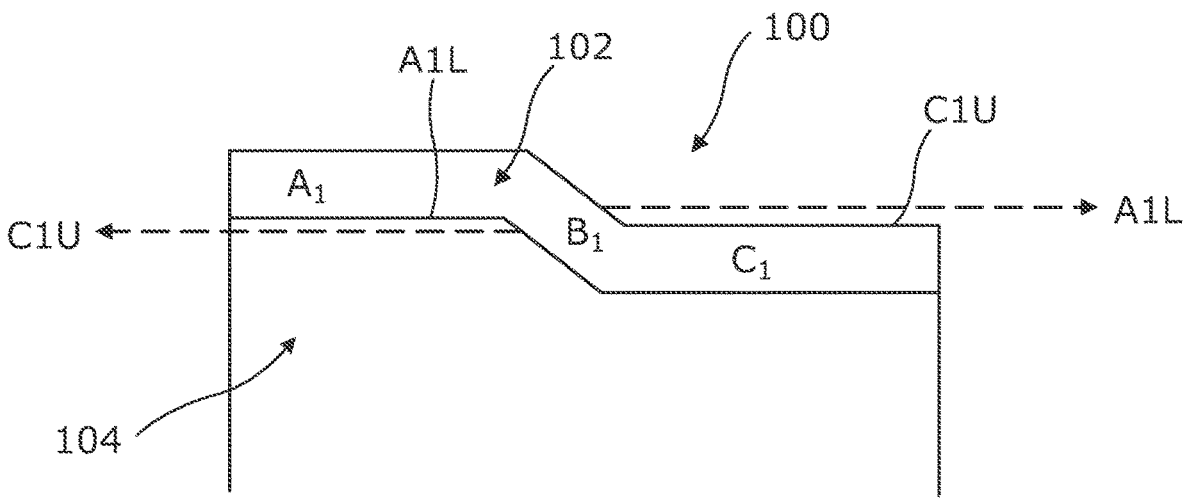
FIG. 4 shows a further horizontal plane view of the garter, band or cuff in the sock garment of the present invention in one embodiment.

Referring to FIG. 4, in order to prevent any inadvertent 360 degree circumferential force being applied by the cuff, band or garter 102, the lowest edge (A1L) of the anterior portions (A1) (or the edge of the anterior portions furthest from the knee) is separated from the highest edge (C1U) of the posterior portions (C1) (or the edge of the posterior portions closest to the knee) such that the edges A1L and C1U are not in the same horizontal anatomical plane or at the same height when the garment is worn by a user in use.

In one example, the distance between the anterior portion edge A1L and the posterior portion edge C1U is equal to or greater than 1 mm.

Figure 5:
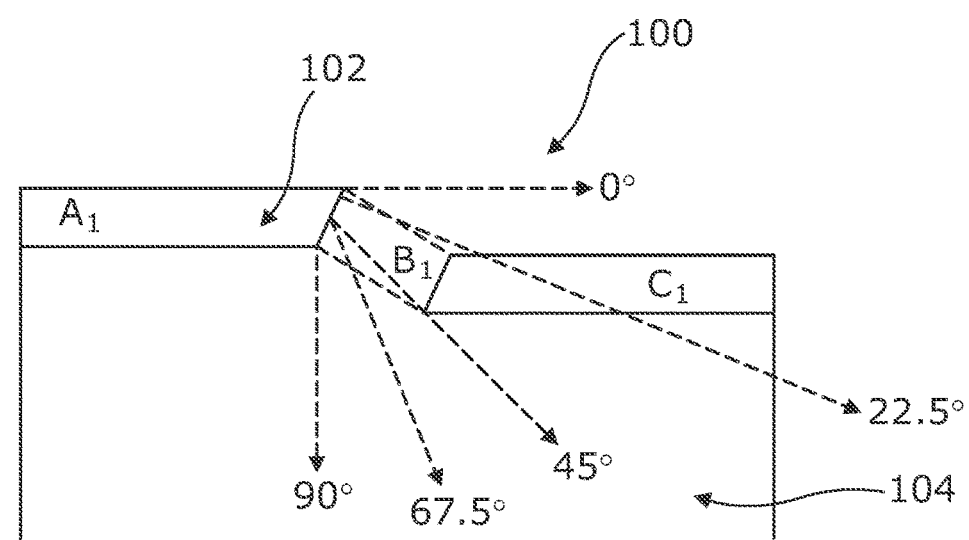
FIG. 5 shows examples of the angles of the intermediate portions of the garter, band or cuff with respect to the anterior portions in one embodiment.

FIG. 5 shows examples of the angles of the intermediate portion B1 of the garter, band or cuff 102 with respect to the anterior portion A1 in one embodiment. Fr example, the handle of the intermediate portion B1 could be 22.5 degrees, 45 degrees, 67.5 degrees or any suitable angle therebetween.

Figure 6:
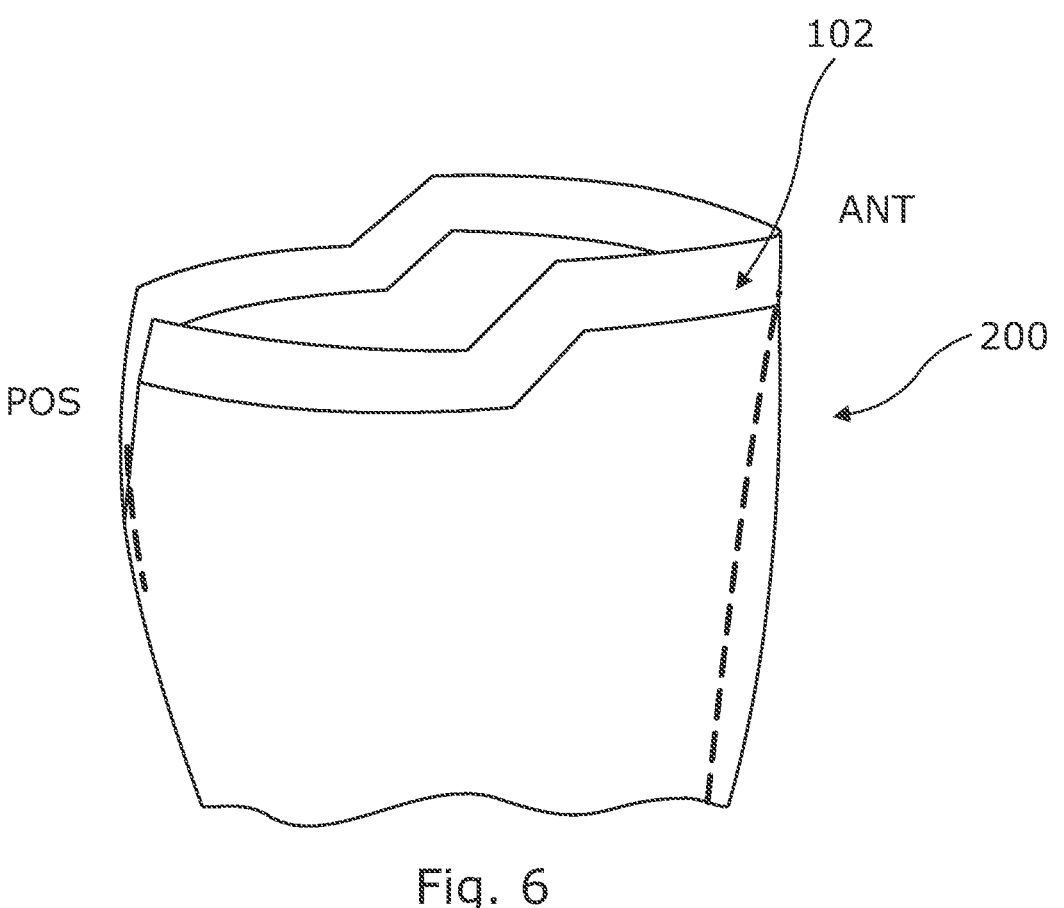
FIG. 6 is an example of a garment in the form of a sock or calf sleeve incorporating the present invention in one embodiment.
Figure 7:
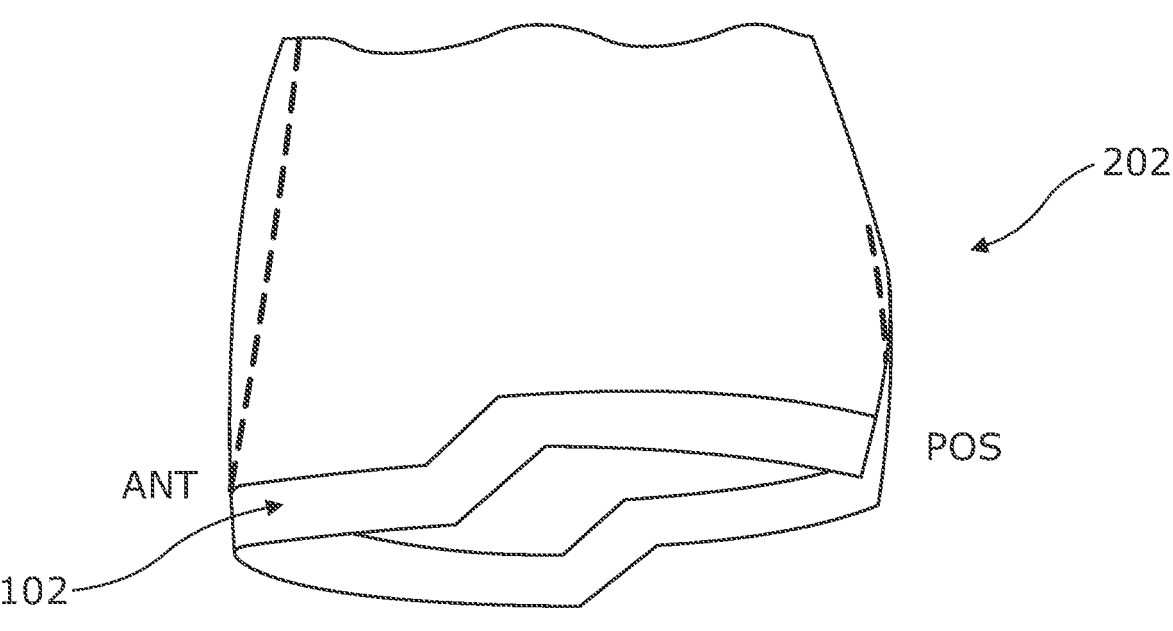
FIG. 7 is an example of a garment in the form of a pair of shorts (only one leg of the shorts is shown for clarity purposes) incorporating the present invention in one embodiment.
Figure 8:
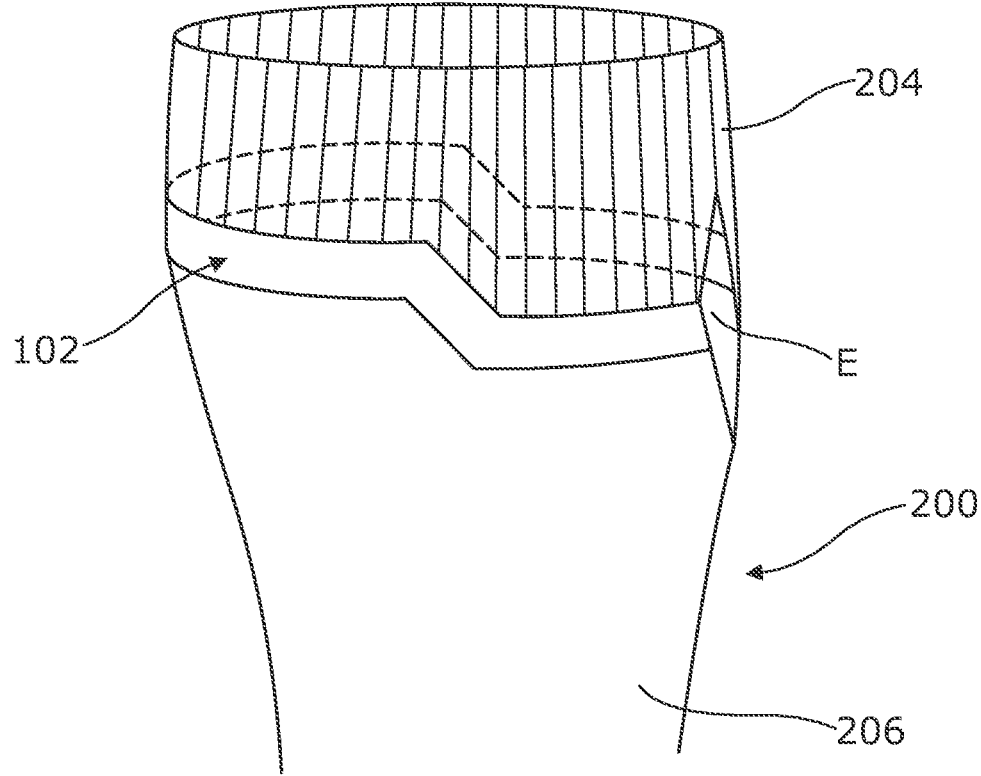
FIG. 8 is an example of a garment in the form of a sock according to a further embodiment of the present invention.
Figure 9:
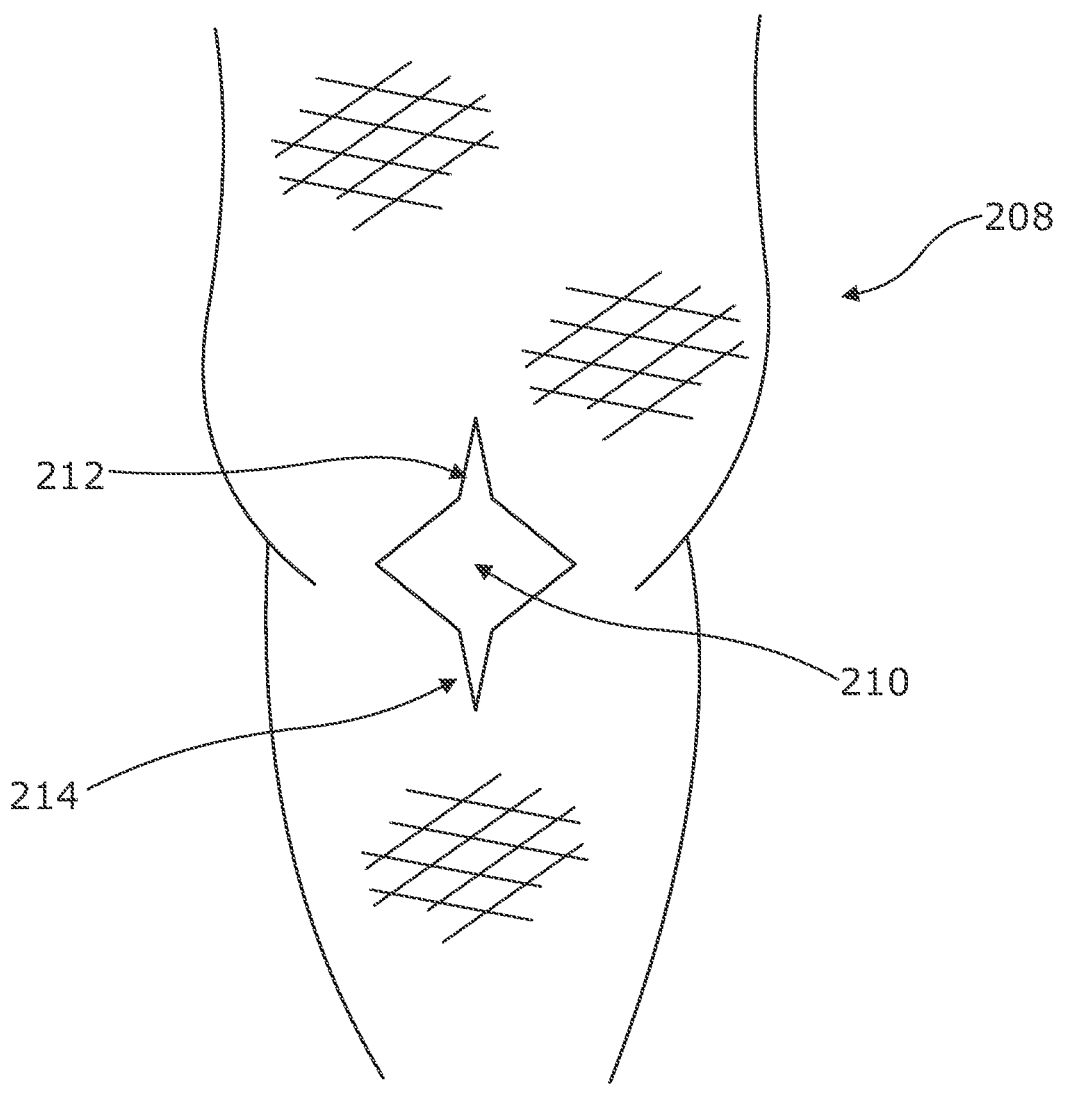
FIG. 9 is an example of a garment in the form of tights (only one leg of the tights is shown for clarity purposes) according to an embodiment of the present invention.

It will be appreciated that the garment incorporating the inventive feature or features of the present invention can take a number of different possible forms. The anterior of the garment is marked with 'ANT' and the posterior of the garment is marked 'POS'. For example, in FIG. 6, the garment is in the form of a sock 200 with a garter 102 providing an area of increased compressive force arranged at the top of the sock nearest to a wearer's knee when the sock is worn. In FIG. 7, the garment is in the form of a pair of shorts 202 with a garter 102 providing an area of increased compressive force arranged at a base of the shorts. In FIG. 8, the garment is in the form of a sock 200 but in this embodiment material is provided above the garter 102. The material of the sock provided above 204 and/or below 206 the garter typically provides a different level of compressive force or a much lower level of compressive force compared to the garter itself. In one example, the notch, aperture or cut out 'E' can be diamond shaped, or a similar or same notch or space above the garter 102 can be provided to a notch or space below the garter 102. The material 204 above the garter 102 could be folded over the garter region, thereby having the appearance of the sock in FIG. 6 in one example. This may happen, for example, if the socks are football socks. In an alternative example, no space or notch 'E' is provided in the material 204 above the garter 102 and so if it is folded over the garter in use, the space or notch 'E' is no visible.

It will be appreciated that some garments do not have a cuff, garter or band around the knee area but none the less provide compressive force over, above and/or below the knee as a result of material of the garment covering the knee. This is the case in garments such as stockings, tights, figure hugging athletic wear, shapewear and/or the like. In this example of tights 208, a notch 210, preferably which is diamond shaped, is defined in the posterior region of the knee adjacent the popliteal fossa located at the back of a knee of a human subject. Further openings or notches 212, 214 can be provided in the superior aspect and inferior aspect of the notch 210. The diamond shape is designed to reflect the shape of the popliteal area of the knee where highly vulnerable neurovascular structures are present. The notch or gap significantly reduces the compressive forces present in the popliteal area of a user's knee in use.

The further inferior and/or superior notches remove further circumferential pressure on the neurovascular structures at the lower aspect of the knee and/or upper aspect of the calf, or the upper aspect of the knee and/or lower aspect of the thigh, areas of which have been shown to be vulnerable to external compressive material forces. Other benefits include a reduction of material rolling or sagging in the posterior region of the knee, increased ventilation, reduction of bacterial and/or fungal infections and/or the like.

A further set of conventional garments may include both a cuff, band or garter and material coverage over the knee, such as for example, ¾ length tights, knee supports and/or the like.

Figures 10A, 10B:
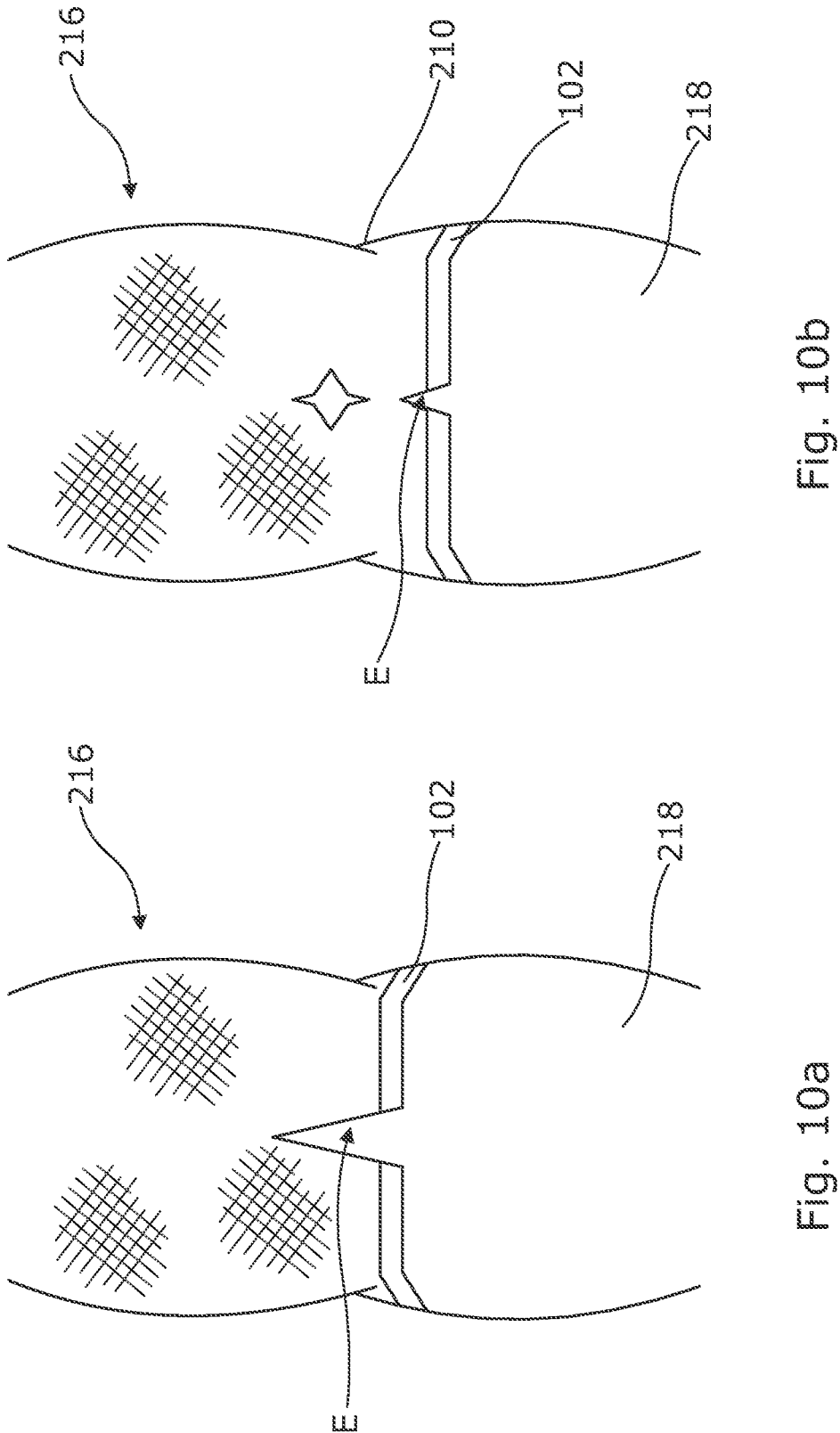
FIGS. 10a and 10b are examples of a garment in the form of ¾ length tights showing different embodiments of the present invention.

FIG. 10a shows one leg 216 of a pair of ¾ length tights worn on a user's leg 218 according to an embodiment of the present invention. The material of the tights extends over the knee and the garter 102 of the tights sits immediately below the knee is use. A V-shaped notch 'E' can be provided in the posterior region of the knee as previously described. In FIG. 10b, a diamond shaped notch 210 can be provided alone or in combination with a V-shaped notch 'E'. When a diamond shape notch 210 is used in combination with a V-shaped notch 'E', the two notches are provided a spaced distance apart from each other and the V-shaped notch is typically of smaller dimensions that if a V-shaped notch alone was to be used.

Figures 11A, 11B:
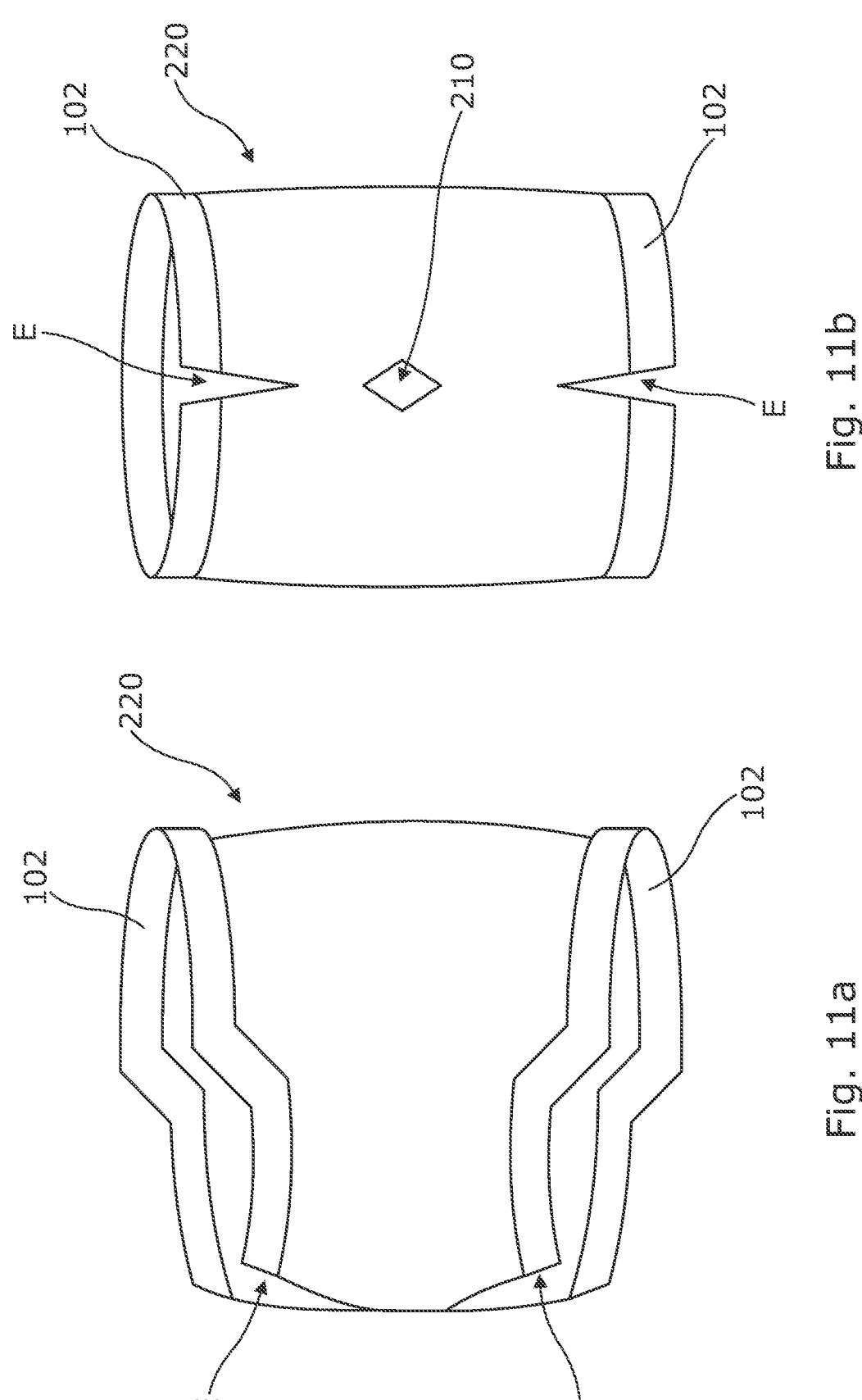
FIGS. 11a and 11b are examples of a garment in the form of strapless knee supports showing different embodiments of the present invention.

FIGS. 11a and 11b show examples of a strapless knee support 220 according to embodiments of the present invention, which typically has garters 102 above and below the knee when worn by a user in use. In FIG. 11a, a V-shaped notch is provided in both the upper and lower garters 102. The apexes of the V-shaped notches typically face towards each other. In FIG. 11b, a diamond shaped notch 210 is provided in the posterior aspect of the knee support and V-shaped notches are provided in the upper and lower garters 102.

Figure 12A:
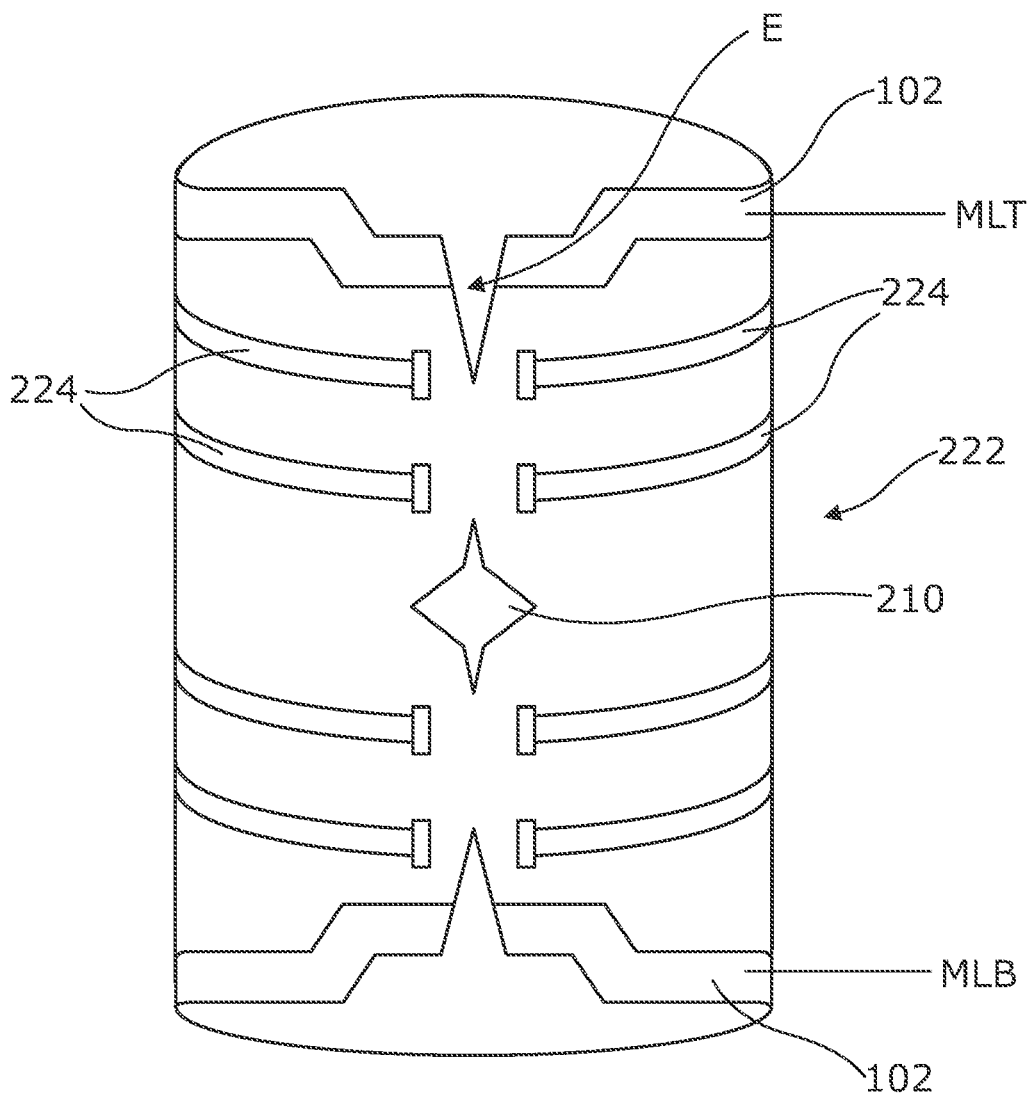
FIGS. 12a and 12b show a posterior view and an anterior view respectively of an example of a garment in the form of a knee support with straps according to an embodiment of the present invention.
Figure 12B:
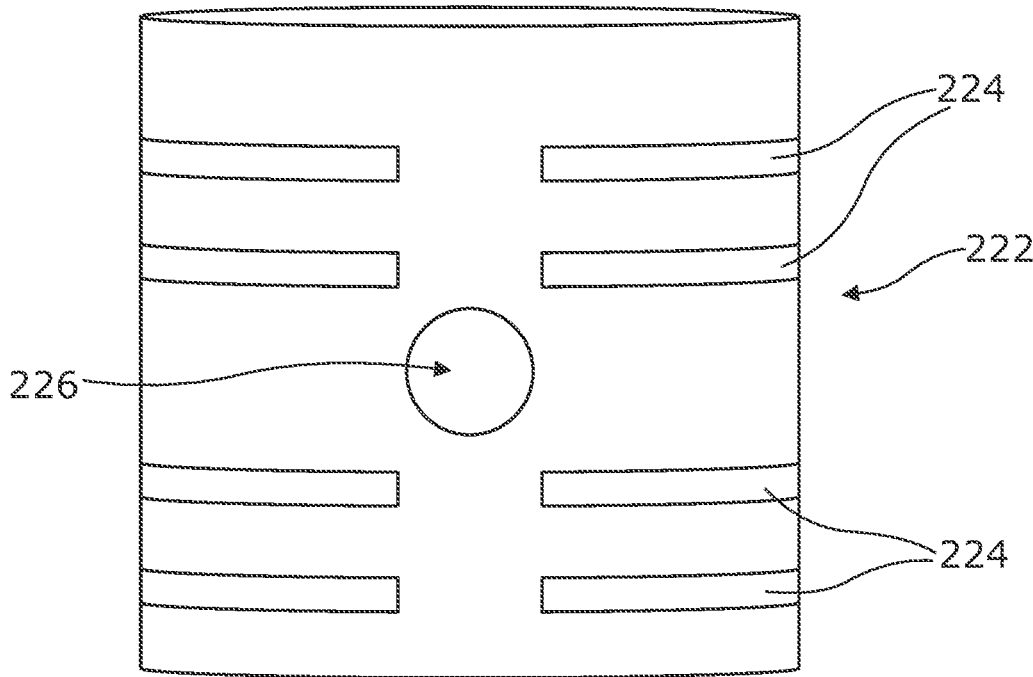

FIGS. 12a and 12b show an example of a strapped knee support 222 in a posterior view and anterior view respectively, according to embodiments of the present invention. The support 222 typically includes a plurality of adjustable straps 224 that can be adjusted via a variety of different means, such as for example, via buckles, ratchet mechanism hook and loop fastenings (VELCRO) and/or the like. In FIGS. 12a and 12b, the support 222 is provided with a compressive garter 102 on both the upper and lower edges of the support. A V-shaped notch 'E' can be provided in each garter 102 as previously described. A diamond shaped notch 210 can be provided at the posterior part of the garment as previously described. No straps are provided at or immediately adjacent the notch 210 to remove the risk of too much compression in the posterior area of the knee in use. In addition, it is to be noted that no straps are provided in the posterior mid region of the support 222 along the vertical or upright axis, thereby ensuring that posterior compression is reduced. An aperture 226 is defined in the anterior of the support 222, as shown in FIG. 12b. It will be appreciated that reinforcing rib or support members may be provided in the knee support 222 as required. In one embodiment, the notch, aperture or cut-out or stepped nature of the cuff, garter or band in the garment provides no compressive force in at least the posterior region of the knee of the user or the compressive force applied to the posterior region of the knee of the user is less than or equal to about 8 mmHg, and preferably less than or equal to about 7 mmHg, 6 mmHg, or 5 mmHg.

REFERENCES

Buhs, C. L., Bendick, P. J & Gover, J. L. [1999]. The effect of graded compression elastic stockings on the lower leg venous system during daily activity. Journal of Vascular Surgery Campion, E. C., Hoffman, D. C. & Jepson, R. P. [1968]. The Effects of External Pneumatic Splint Pressure on Muscle Blood Flow. Australia & New Zealand Journal of Surgery 38[2]. 154-157.

Couzan, S., Leizorovicz, A., Laporte, S, Mismetti, P, Pouget, J, Chapelle & Quere, I. [2012]. A Randomized double-blind trial of upward progressive versus degressive compressive stockings in patients with moderate to severe chronic venous insufficiency. Journal of Vascular Surgery 56[5]. 1334-1350.

Dermont, T, Morizot, L, Bouhaddi, M & Menetrier, A. [2015]. Changes in Tissue Oxygen Saturation in Response to Different Calf Compression Sleeves. Journal of Sports Medicine. Hindawi Publishing Corporation. 1-5.

Fromy, B, Legrand, M. S. Abraham, P, Leftheriotis, G, Cales, P & Saumet, J. L. [1997]. Effects of positive Pressure on Both Femoral Venous and Arterial Blood Velocities and the Cutaneous Microcirculation of the Forefoot. Cardiovascular Research, 36, 372-376.

Gaylarde, P. M, Sarkany, I & Dodd, H. J. [1993]. The Effect of Compression on Venous Stasis. British Journal of Dermatology, 128, 255-258.

Husni, E. A, Ximenes, J. O. C & Hamilton, F. G. [1968]. Pressure Bandaging of The Lower Extremity, Use and Abuse. JAMA, 206[12], 2715-2718.

Kamm, R. D. [1982]. Bioengineering studies of Periodic External Compression as Prophylaxis Against Deep Vein Thrombosis—Part 1: Numerical Studies. Journal of Bio-mechanical Engineering, 104, 87-95.

Lewis, C. E, Antione, J, Mueller, C, Talbot, W. A, Swaroop, R & Edwards, W. S. [1976]. Elastic Compression in the Prevention of Venous Stasis. A Critical Re-evaluation. The American Journal of Surgery, 132, 739-743.

Lim, C. S & Davies, A. H. [2014]. Graduated Compression Stockings. Journal of Canadian Medical Association, 186 [10], 391-398.

Litter, J & Wood, J. E. [1954]. The Volume and Distribution of Blood in the Human Leg Measured In Vivo. The Effects of Graded External Pressure. Journal of Clin Invest, 33[5], 798-806.

Lord, R. S. A & Hamilton, D. [2004]. Graduated Compression Stockings (20-30 MMHG) Do Not Compress Leg Veins In The Standing Position. ANZ Journal of Surgery, 74, 581-585.

Mayrovitz, H. N. [1998]. Simultaneous Changes in Leg Arterial Pulsatile Blood Flow and Toe Laser-Dopler Perfusion Accompanying Graded Thigh Compression. Vascular Surgery, 32[4], 329-338.

Mayrovitz, H. N & Sims, N. [2003]. Effects of Ankle to Knee External Pressures on Skin Blood Perfusion Under and Distal to Compression. Advanced Skin Wound Care, 16, [4], 198-202.

Merrett, N. D & Hanel, K. C. [1993]. Ischaemic Complications of Graduated Compression Stockings in the Treatment of Deep Vein Thrombosis. Journal of Post Graduate Medicine, 69, 232-234.

Mosti, G & Partsch, H. [2011]. Compression Stockings with a Negative Pressure Gradient Have a More Pronounced Effect on Venous Pumping Function than Graduated Elastic Compression Stockings. European Journal Vascular Endovascular Surgery, 42, 261-266.

Partsch, B & Partsch, H. [2005]. Calf compression pressure required to achieve venous closure from supine to standing positions. Journal of Vascular Surgery, 42, 734-738.

Sabri, S, Roberts, V. C & Cotton, L. T. [1971]. Effects of Externally Applied Pressure on the Haemodynamics of the Lower Limb. British Medical Journal, 3, 503-508.

Scurr, J. H, Machin, S. J. Bailey-King, S, Mackie, I. J, Macdonald, S & Smith, P. D. [2001]. Frequency and Prevention of Symptomless Deep-Vein Thrombosis in Long-Haul Flights: A Randomized Trial. Lancet, 357 [9267], 1485-1489.

Sigel, B, Edelstein, A. L, Savitch, L, Hasty, J. H & Felix, R. [1975]. Type of Compression for Reducing Venous Stasis: A Study of Lower Extremities During Inactive Recumbency. Arch Surgery, 110, 171-175.

Spiro, M, Roberts, V. C & Richards, J. B. [1970]. Effect of Externally Applied Pressure on Femoral Vein Blood Flow. British Medical Journal, 1, 719-723.

Thirsk, R. B, Kamm, R. D & Shapiro, A. H. [1980]. Changes in Venous Blood Volume Produced by External Compression of the Lower Leg. Med. & Biol. Eng. & Compute, 18, 650-656.

Zicot, M, Parker, K. H & Caro, C. G. [1977]. Effect of Positive External Pressure on Calf Volume and Local Venous Haemodynamics. Phys. Med. Biol, 22[6], 1146-1159.

SEQUENCE LISTING

Not Applicable.

The invention claimed is:

1. A garment; at least part of said garment is arranged to be worn on a lower limb of a human subject and to cover a knee of the lower limb of the human subject or be provided at, above or below the knee of the lower limb of the human subject in use; at least one section of said garment is arranged to provide a compressive force to one or more locations on the lower limb of the human subject when worn in use; characterised in that:

the garment is arranged such that the part of said garment that covers said knee or is provided at, above or below the knee when the garment is worn in use has at least one region that applies no compressive force to the venous vessels at, above, or below the knee of the human subject when the garment is worn by the subject; or any compressive force that is applied by the garment to the venous vessels at, above, or below the knee of the human subject when the garment is worn is less than 8 mmHg;

wherein:

a) the at least one region is a posterior region of the garment and includes at least one notch, aperture, or cut-out in the material of the garment;

b) the garment includes a stepped cuff, band, or garter that is to be worn on the lower limb of the human subject in use, and the at least one region of the garment includes a first portion of the cuff, band, or garter in a posterior region of the garment that is further away from the knee compared to a second portion of the cuff, band, or garter in an anterior region of the garment based on anatomical height of the human subject when the garment is worn in use; and/or c) the number, orientation, density, and/or tightness of fibres of material of the garment provide the required compressive force in the garment.

2. The garment according to claim 1, wherein the garment is arranged such that any compressive force that is applied by the garment in the at least one region to the venous vessels at, above, or below the knee when the garment is worn in use is less than or equal to 7 mmHg, 6 mmHg, or 5 mmHg.

3. The garment according to claim 1, wherein the anterior region of the garment is arranged to provide the compressive force or a relatively greater compressive force to an anterior area of the subject's knee relative to the compressive force provided by the posterior region of the garment at a posterior area of the subject's knee at the same circumferential or anatomical height or distance at, above and/or below the subject's knee in use.

4. The garment according to claim 1, wherein the second portion of cuff, band or garter provides a compressive force or a relatively greater compressive force compared to the first portion of the cuff, band or garter.

5. The garment according to claim 1, wherein the cuff, band or garter is continuous or substantially continuous in perimeter or circumference of the garment.

6. The garment according to claim 1, wherein the at least one notch, aperture or cut-out also extends beyond the cuff, the band or the garter.

7. The garment according to claim 1, wherein at least part of the notch, aperture or cut-out defined in the garment is shaped such that it has a narrowing taper in a direction away from the knee region of the garment or away from the subject's knee when the garment is worn in use and/or is diamond shaped, substantially diamond shaped, V-shaped, substantially V-shaped, U-shaped or substantially U-shaped.

8. The garment according to claim 1, wherein the cuff, the band or the garter includes two or more anterior portions located in the anterior region of the garment that are arranged to be on opposing but equal or substantially equal anatomical plane heights of the human subject when the garment is worn in use and are located in an anterior area of the subject's knee; and two or more posterior portions located in the posterior region of the garment that are arranged to be on opposing but equal or substantially equal anatomical plane heights when the garment is worn in use and are located in a posterior area of the subject's knee; and wherein the anterior portions are closer to the knee of the garment compared to the posterior portions or are provided at different anatomical plane heights when the garment is worn in use.

9. The garment according to claim 8, wherein the cuff, the band or the garter includes two or more intermediate portions that are located intermediate the anterior and posterior portions on opposing sides of the garment; and the two or more intermediate portions are arranged to be at equal or substantially equal anatomical plane heights when the garment is worn in use, are provided at the same angle relative to the respective anterior or posterior portion, are angulated obliquely to provide a step change in the anatomical plane height between the anterior and posterior portions, or are provided at an angle of 20-70 degrees+/−5 degrees relative to an edge of the anterior portion closest to the knee region of the garment in use.

10. The garment according to claim 8, wherein the two or more posterior portions do not join together and are a spaced distance apart from each other to define the notch, aperture or cut-out therebetween.

11. The garment according to claim 1, wherein the notch, aperture or cut-out defined in the garment does not have any material in, associated with or over the same; wherein the notch, aperture or cut-out has material in, associated with or over the same but said material provides no compressive force, or provides the compressive force of less than 8 mmHg.

12. The garment according to claim 1, wherein an interior or superior aspect of the notch, aperture or cut-out has at least one further notch defined in the same; or an inferior or superior aspect of the notch, aperture or cut-out extends a greater distance in the respective interior or superior directions of the garment than the notch, aperture or cut-out extends in the proximal or lateral aspects.

13. The garment according to claim 1, wherein the notch, aperture or cut-out of the garment is covered or substantially covered by a material that is different to the material of the garment in which the notch, aperture or cut-out is defined.

14. The garment according to claim 1, wherein the at least one section of the garment providing the compressive force is formed from or includes any or any combination of: a material that can generate a compressive force when the garment is worn by the subject in use, elastic fibre material, Lycra®, cotton, synthetic material, elastic composite material or is able to exert a pressure on average of less than or equal to 8 mmHg.

15. The garment according to claim 1, wherein the garment is any of a sock; a compression sock; a calf muscle sleeve, support or brace; a knee sleeve, support or brace; a thigh sleeve, support or brace; a lower limb sleeve, support or brace, a lower limb stocking, tights, body suit, body suit, tri-suit or shorts.

*   *   *   *   *